(12) United States Patent
Gittard et al.

(10) Patent No.: US 9,615,880 B2
(45) Date of Patent: Apr. 11, 2017

(54) ABLATION MESH

(71) Applicant: Cook Medical Technologies LLC, Bloomington, IN (US)

(72) Inventors: Shaun D. Gittard, Winston-Salem, NC (US); Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 336 days.

(21) Appl. No.: 14/327,239

(22) Filed: Jul. 9, 2014

(65) Prior Publication Data

US 2015/0025531 A1   Jan. 22, 2015

Related U.S. Application Data

(60) Provisional application No. 61/847,416, filed on Jul. 17, 2013.

(51) Int. Cl.
| | |
|---|---|
| *A61B 18/12* | (2006.01) |
| *A61B 18/14* | (2006.01) |
| *A61B 18/00* | (2006.01) |

(52) U.S. Cl.
CPC .. *A61B 18/1492* (2013.01); *A61B 2018/0016* (2013.01); *A61B 2018/0022* (2013.01);
(Continued)

(58) Field of Classification Search
CPC ...... A61B 18/1492; A61B 2018/00077; A61B 2018/0016; A61B 2018/00214;
(Continued)

(56) References Cited

U.S. PATENT DOCUMENTS

| | | | | |
|---|---|---|---|---|
| 4,337,223 A | * | 6/1982 | Kaye | A61L 2/206 422/112 |
| 4,920,978 A | * | 5/1990 | Colvin | A61N 1/403 600/549 |

(Continued)

OTHER PUBLICATIONS

International Search Report mailed Oct. 20, 2014 for International Application No. PCT/US2014/045864.
(Continued)

*Primary Examiner* — Daniel Fowler
(74) *Attorney, Agent, or Firm* — Brinks Gilson & Lione (57) ABSTRACT

An ablation device and a method of ablating a tissue are provided. The ablation device includes a tubular member having a proximal portion, a distal portion, a lumen extending at least partially therethrough and a conductive portion. The tubular member has a first configuration and a second configuration. The ablation device includes a distal cap operably connected to the distal portion having a diameter that is smaller than a diameter of a distal end portion of an endoscope and a proximal ring connected to the proximal portion having a diameter greater than a diameter of the distal end portion. The ablation device also includes a first catheter operably connected to the distal cap and a second catheter operably connected to the proximal ring, where the proximal ring is movable relative to the distal cap to move the tubular member between the first configuration and the second confirmation.

20 Claims, 7 Drawing Sheets

(52) U.S. Cl.
CPC ............... *A61B 2018/00077* (2013.01); *A61B 2018/00214* (2013.01); *A61B 2018/00267* (2013.01); *A61B 2018/00434* (2013.01); *A61B 2018/00494* (2013.01)

(58) Field of Classification Search
CPC .. A61B 2018/0022; A61B 2018/00267; A61B 2018/00434; A61B 2018/00494; A61B 2017/00292; A61B 2017/00296; A61B 1/00085; A61B 1/00101
See application file for complete search history.

(56) References Cited

U.S. PATENT DOCUMENTS

| | | | | |
|---|---|---|---|---|
| 5,540,658 | A * | 7/1996 | Evans | A61B 17/42 604/101.04 |
| 5,569,241 | A * | 10/1996 | Edwards | A61B 18/148 604/22 |
| 5,653,684 | A * | 8/1997 | Laptewicz | A61B 18/1492 604/107 |
| 5,868,708 | A * | 2/1999 | Hart | A61M 25/1002 604/101.05 |
| 5,925,038 | A | 7/1999 | Panescu et al. | |
| 6,315,778 | B1 * | 11/2001 | Gambale | A61B 18/1492 606/41 |
| 7,255,695 | B2 | 8/2007 | Falwell et al. | |
| 7,489,969 | B2 | 2/2009 | Knudson et al. | |
| 7,667,750 | B2 | 2/2010 | Goto et al. | |
| 8,249,685 | B2 * | 8/2012 | Falwell | A61B 18/1492 600/373 |
| 2004/0181139 | A1 * | 9/2004 | Falwell | A61B 5/0422 600/374 |
| 2010/0145327 | A1 | 6/2010 | Thompson et al. | |
| 2010/0160906 | A1 | 6/2010 | Jarrard | |
| 2012/0101413 | A1 | 4/2012 | Beetel et al. | |

OTHER PUBLICATIONS

Written Opinion mailed Oct. 20, 2014 for International Application No. PCT/US2014/045864.

* cited by examiner

ABLATION MESH

RELATED APPLICATIONS

This application claims the benefit of U.S. Provisional Application No. 61/847,416, filed Jul. 17, 2013, which is incorporated by reference herein in its entirety.

BACKGROUND

Altering the activity of nerves to modulate physiological processes in the body is an approach that is increasing in use. For example, denervation of the renal nerves has been used to decrease blood pressure. Stimulation of nerves has also been used to modulate physiological processes. Interruption of the electrical activity of the vagal nerve has been utilized to treat obesity and diabetes as disclosed in U.S. Pat. Nos. 7,167,750 and 7,489,969.

The nervous system of the gastrointestinal tract includes three types of nerve systems: the intrinsic system, the sympathetic extrinsic system and the parasympathetic extrinsic system. The intrinsic nerves send signals within the digestive system. The extrinsic nerves (both sympathetic and parasympathetic) communicate between the digestive system and other organs outside of the digestive tract. Both stimulating and suppressing the signal of these nerves can alter physiological processes related to metabolism. For example, altering the signal of the nerves that are innervating to the gastrointestinal system can change how the gastrointestinal system is absorbing and moving food. Likewise, altering the signal of nerves that are innervating away from the gastrointestinal system can change how other organs involved in metabolism react. Examples include altering pancreatic or biliary secretions or mental feeling of satiety.

Current treatments for ablation of tissues in the gastrointestinal system include bipolar probes, needle knives, sphincterotomes, snares and balloons. However, these current devices do not treat large ablation areas.

What is needed in the art are devices and methods for altering the electrical activity of nerves in the gastrointestinal tract and in some embodiments, devices and methods for altering the activity of nerves in the duodenum. The devices and methods disclosed herein may be used for treating metabolic and digestive disorders, such as, but not limited to diabetes, obesity, Krohn's disease and motility disorders.

BRIEF SUMMARY

Accordingly, it is an object of the present invention to provide a device and a method having features for altering the electrical activity of nerves in the gastrointestinal tract and that is suitable for treatment of a large area within the gastrointestinal tract.

An ablation device and a method of ablating a tissue are provided. The ablation device includes a tubular member having a proximal portion, a distal portion, a lumen extending at least partially therethrough and a conductive portion. The tubular member has a first configuration and a second configuration. The ablation device includes a distal cap operably connected to the distal portion having a diameter that is smaller than a diameter of a distal end portion of an endoscope and a proximal ring connected to the proximal portion having a diameter greater than a diameter of the distal end portion. The ablation device also includes a first catheter operably connected to the distal cap and a second catheter operably connected to the proximal ring, where the proximal ring is movable relative to the distal cap to move the tubular member between the first configuration and the second confirmation.

DETAILED DESCRIPTION

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the ablation device to a patient. Hence the term "distal" means the portion of the ablation device that is farthest from the physician and the term "proximal" means the portion of the ablation device that is nearest to the physician.

Figure 1:
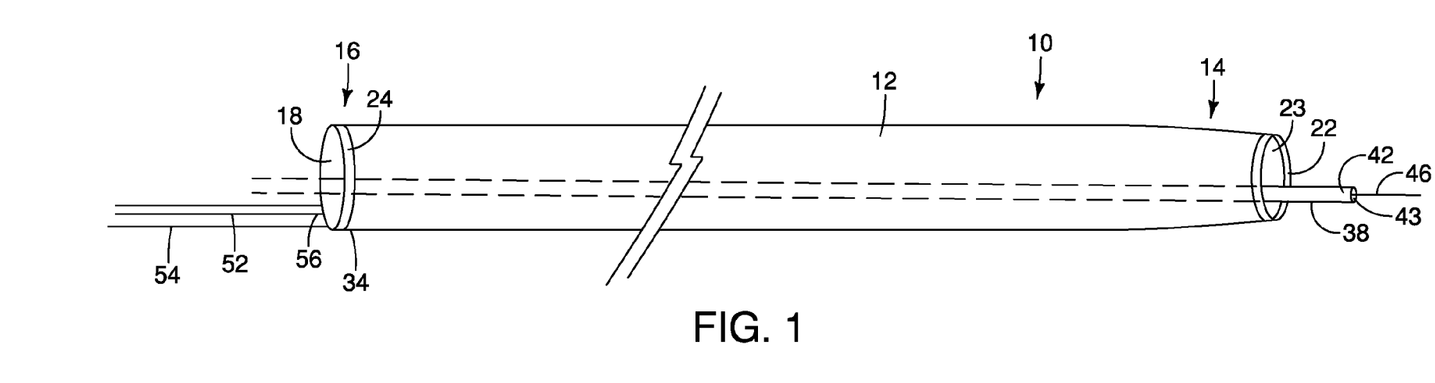
FIG. 1 is a side view of an ablation device in accordance with an embodiment of the present invention.
Figure 2:
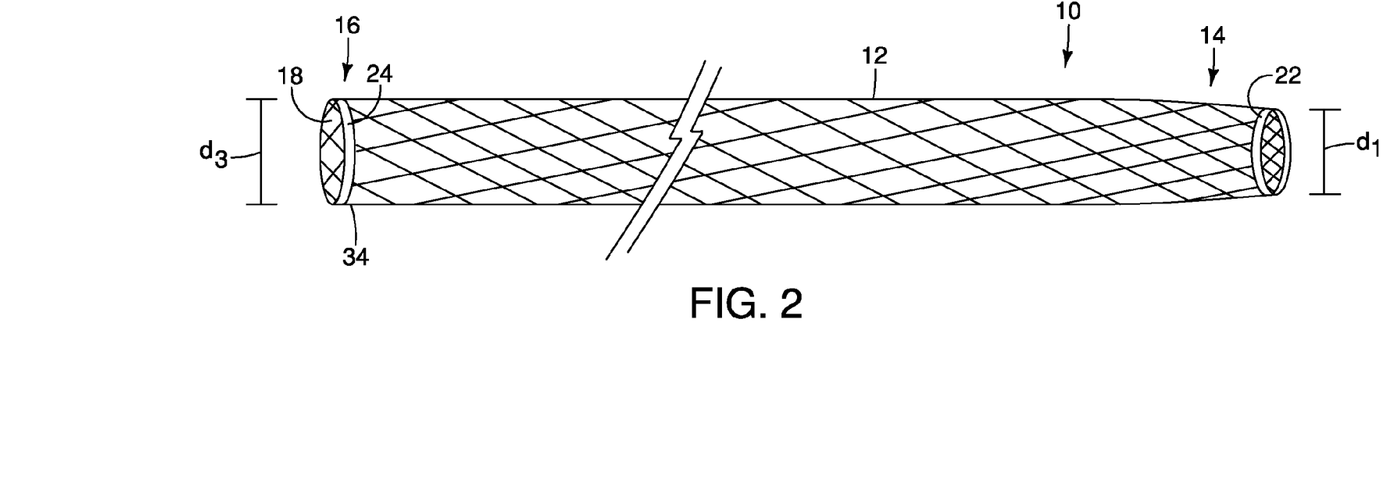
FIG. 2 is side view of the ablation device shown in FIG. 1 showing a mesh.

FIGS. 1 and 2 illustrate an embodiment of an ablation device 10 in accordance with the present invention. The ablation device 10 includes a tubular member 12 having a distal portion 14 and a proximal portion 16. In some embodiments, the tubular member 12 may be formed from a mesh. FIG. 1 illustrates the tubular member 12 that may be configured to include a mesh without showing the mesh pattern to illustrate additional elements of the ablation device 10. FIG. 2 illustrates an embodiment of the tubular member 12 showing an exemplary mesh pattern. The mesh pattern may be varied, for example by changing the density of the weave pattern or the thickness of the woven portions based on the amount of expansion for the tubular member 12. By way of non-limiting example, the tubular member 12 may be expandable to about 3 cm in diameter when the tubular member 12 is configured for use in the duodenum. Other diameters are also possible and will depend on the location of the body lumen where the tubular member 12 will be used. A lumen 18 extends longitudinally through the tubular member 12. The ablation device 10 may further include a distal cap 22. The distal cap 22 connects to a distal end 28 of the tubular member 12. The distal cap 22 includes an opening 23 having a diameter $d_1$. The distal cap 22 is configured to prevent the distal end 28 of the tubular member 12 from moving proximally over an endoscope as described in more detail below. The ablation device 10 also may include a proximal ring 24 at a proximal end 34 of the tubular member 12. The proximal ring may be sized and shaped to surround a distal portion of an endoscope as described below.

Figure 4:
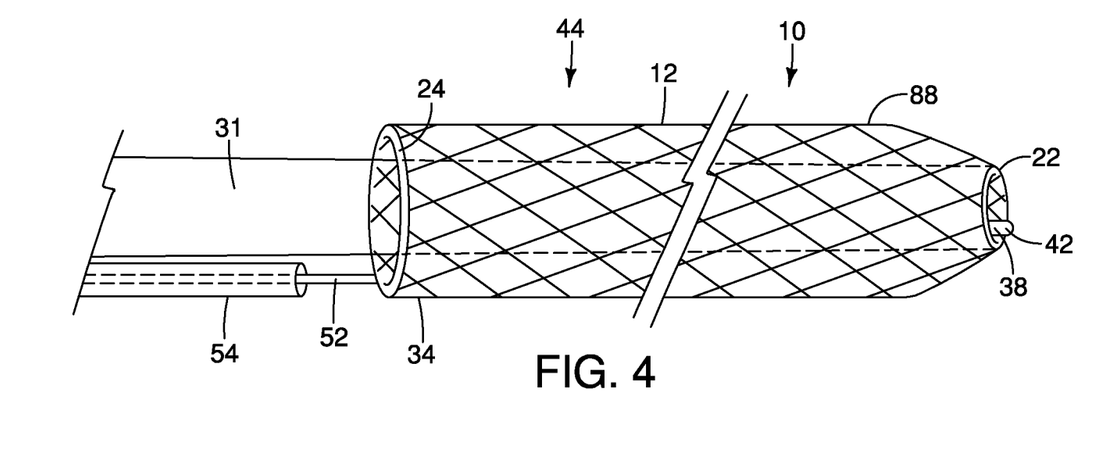
FIG. 4 is a side view of an ablation device positioned over an endoscope in a second configuration.

The ablation device 10 may also include a tensioning catheter 38. In some embodiments, the tensioning catheter 38 extends through the lumen 18 of the tubular member 12 and connects to the distal cap 22. In some embodiments, the tensioning catheter 38 may be positioned external to the tubular member 12. The tensioning catheter 38 maybe positioned at least partially within a working channel of an endoscope and the ablation device 10 positioned over the endoscope as described in more detail below. The tensioning catheter 38 is shown in FIG. 1 with a distal end portion 42 of the tensioning catheter 38 connected to and extending distal to the distal cap 22. In some embodiments, the distal end portion 42 of the tensioning catheter 38 may be connected to and positioned at the distal cap 22 as shown in FIG. 4. The tensioning catheter 38 may include a lumen 43 extending at least partially through the catheter 38. In some embodiments, a wire guide 46 may be extended through the lumen 43 of the tensioning catheter 38 to facilitate positioning of the ablation device 10 within a patient's lumen.

As shown in FIG. 1, the ablation device 10 may also include a pushing catheter 52 and an over catheter 54. A distal end portion 56 of the pushing catheter 52 may be connected to the proximal ring 24. The pushing catheter 52 may be movably positionable through the over catheter 54 so that the pushing catheter 52 can move the proximal ring 24 relative to the distal cap 22. The outer catheter 54 may be positioned outside an endoscope as described in more detail below.

Figure 3A:
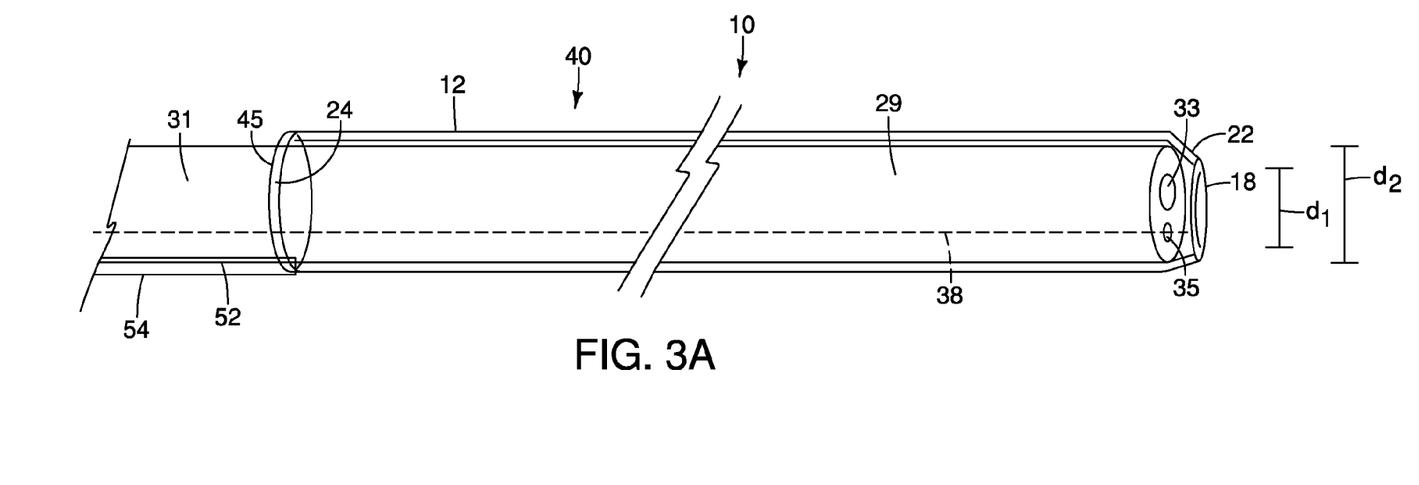
FIG. 3A is a side view of the ablation device shown in FIG. 1 positioned over an endoscope in a first configuration.

FIG. 3A illustrates the ablation device 10 positioned over a distal portion 29 of an endoscope 31. The tubular member 12 may be sized and shaped to fit over the distal portion 29 of the endoscope 31 in a first configuration, 40 so that the tubular member 12 is positioned close to the distal portion 29 of the endoscope 31 and the endoscope 31 can be advanced through a patient's lumen with the ablation device 10 positioned over the distal portion 29 of the endoscope 31. The diameter $d_1$ of the opening 23 of the distal cap 22 is smaller than an outer diameter $d_2$ of the distal portion 29 of the endoscope 31. The distal cap 22 may be configured to prevent the distal cap 22 of the ablation device 10 from moving proximally over the distal portion 29 as the endoscope 31 is advanced into the lumen. The distal cap 22 may be configured so that an optical/lighting channel 33 of the endoscope 31 is unobstructed by the distal cap 22 when the ablation device 10 is positioned over the distal portion 29 of the endoscope 31. The tensioning catheter 38 is shown in FIG. 3A extending through a working channel 35 of the endoscope 31. The distal end portion 42 of the tensioning catheter 38 is connected to the distal cap 22 that is positioned distal to the endoscope 31.

Figure 3B:
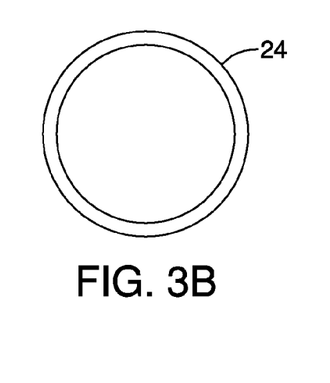
FIG. 3B is a cross-sectional view of a portion of the ablation device shown in FIG. 1.
Figure 3C:
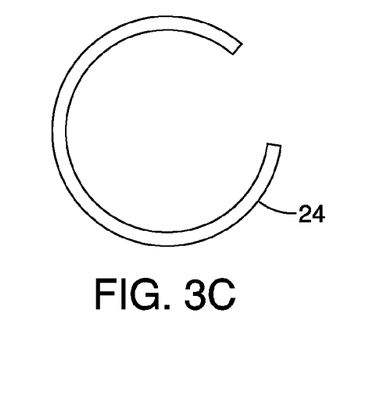
FIG. 3C is an alternative cross-sectional view of the embodiment shown in FIG. 3B.

FIG. 3A illustrates an embodiment of the ablation device 10 where the over catheter 54 is shown positioned external to the endoscope 31 and operably connected thereto. The pushing catheter 52 is shown extending through the over catheter 54 and connected to the proximal ring 24. The pushing catheter 52 may also be used to hold the tubular member 12 against the distal portion 29 of the endoscope 31 as the ablation device 10 is advanced or retracted through a patient's lumen. In some embodiments, the pushing catheter 52 may be used to proximally pull on the proximal ring 24 during advancement and/or retraction of the ablation device 10 in the patient's lumen so that the ablation device 10 is positioned close to the endoscope 31. An opening 45 of the proximal ring 24 has an outer diameter $d_3$ that is greater than the diameter $d_2$ of the distal portion 29 of the endoscope 31 so the proximal ring 24 is movably positionable over the distal portion 29 of the endoscope 31. In some embodiments, the ring 24 surrounds the distal portion 29 of the endoscope 31 forming a circular ring as shown in FIG. 3B. In other embodiments, the proximal ring 24 surrounds a portion of the distal portion 29 of the endoscope 31 without forming a complete circle as shown in FIG. 3C. The tensioning catheter 38 and/or the pushing catheter 52 may be used to hold the ablation device 10 against the endoscope 31 in the first configuration 40 as shown in FIG. 3A. The distal cap 22 may be similarly configured to form a circular ring or an incomplete ring. The tubular member 12 may be radially compressed in the first configuration 40 in some embodiments. In other embodiments, the tubular member 12 may be biased in the first configuration 40.

Figure 5:
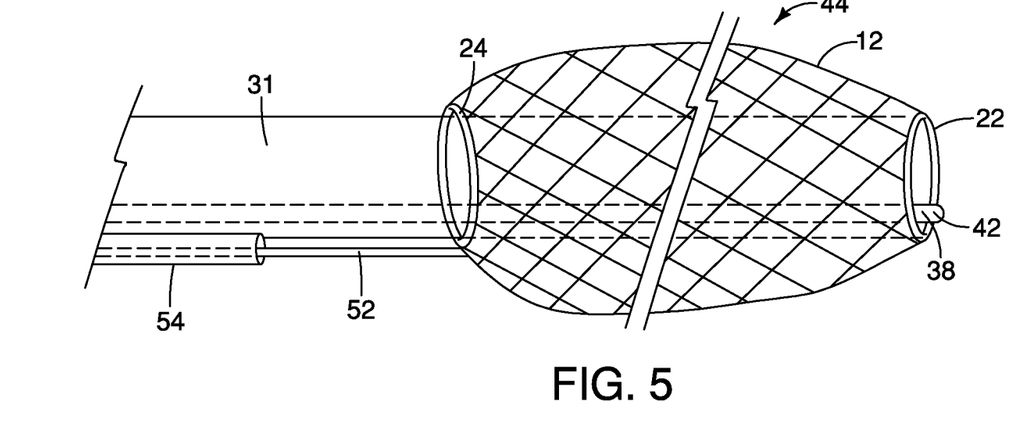
FIG. 5 is a side view of an ablation device positioned over an endoscope in a second configuration.

FIGS. 4 and 5 illustrate the tubular member 12 in a second, expanded configuration 44. As shown, the pushing catheter 52 is advanced distally to move the proximal ring 24 relative to the distal cap 22. The tubular member 12 expands to the second configuration 44 as the proximal ring 24 is moved distally. The second configuration 44 is that is expanded relative to the first configuration 40. The proximal ring 24 may be moved any amount relative to the distal cap 22 to expand the tubular member 12 any amount relative to the first configuration 40. The amount of expansion of the tubular member 12 will depend on the size of the body lumen into which the ablation device 10 is positioned. An exemplary diameter $d_4$ for the expanded configuration 44 is shown in FIG. 5. The pushing catheter 52 and/or the tensioning catheter 38 may be locked in position using a handle (described below) so that the diameter $d_4$ of the tubular member 12 in the expanded configuration 44 may be held constant as the treatment is being delivered to the body lumen. In some embodiments, the size and shape of the body lumen may be increasing or decreasing as the ablation device 10 is advanced so the diameter $d_4$ of the tubular member 12 may be changed during treatment or when the tubular member 12 is positioned at another site. The tubular member 12 may also be locked in the first configuration 40 for delivery to the treatment site and for repositioning.

In some embodiments, the proximal ring 24 may be configured to change in size as the tubular member 12 expands and collapses. For example, in some embodiments, the proximal ring 24 may expand as the pushing catheter 52 advances the proximal ring 24 toward the distal cap 22. In some embodiments, the proximal ring 24 may be made from an elastic material that allows for expansion and contraction of the proximal ring as the tubular member 12 is expanded and contracted. In some embodiments, the incomplete circular proximal ring 24 allows for expansion and contraction with the tubular member 12. The proximal ring 24 may decrease in diameter as the pushing catheter 52 moves the proximal ring 24 proximally relative to the distal cap 22. In some embodiments, the proximal ring 24 remains the same diameter as the proximal ring 24 is advanced and the tubular member 12 expands. In some embodiments, the distal cap 22 may be configured to change diameter when the tubular member 12 is expanded. In some embodiments, the distal cap 22 may be configured to remain the same diameter when the tubular member 12 is expanded and collapsed. In some embodiments, the tubular member 12 may be moved distally and the distal cap 22 may be moved proximally relative to the proximal ring 24 to expand the tubular member 12.

Figure 6:
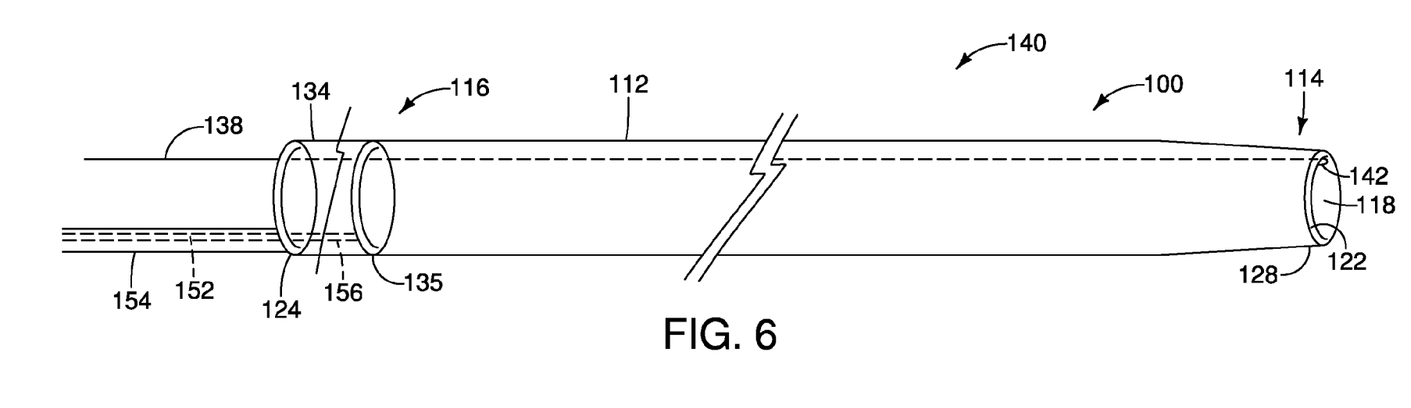
FIG. 6 is a side view of an ablation device positioned over an endoscope in a first configuration.
Figure 7:
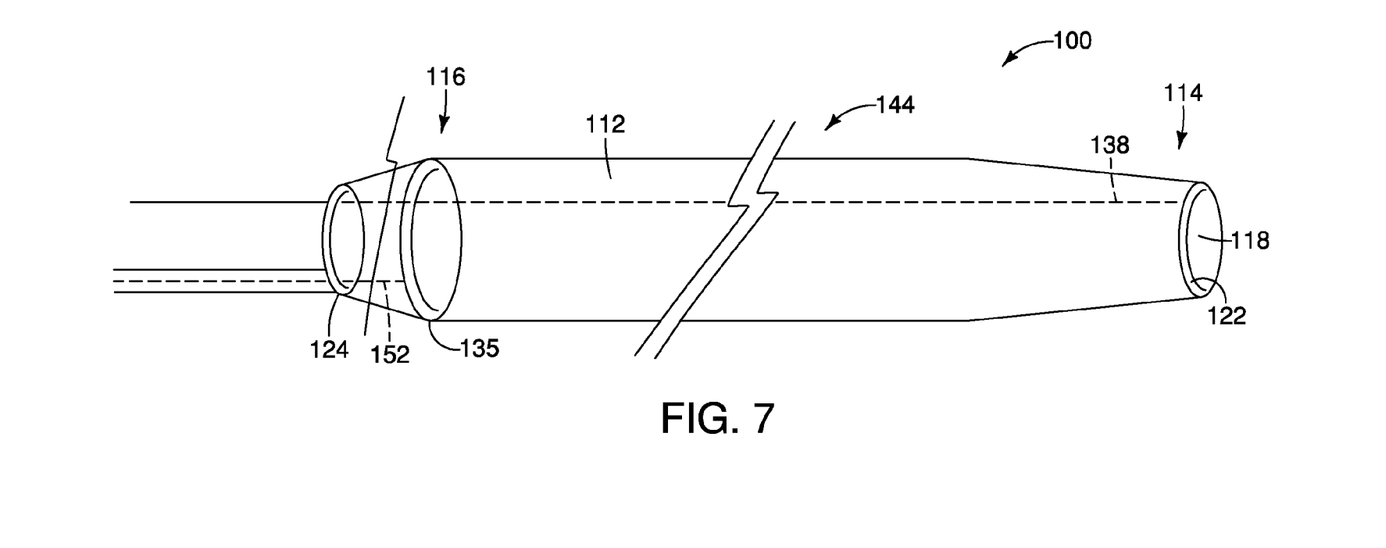
FIG. 7 is a side view of the ablation device shown in FIG. 6 positioned over an endoscope in a second configuration.

FIGS. 6 and 7 illustrate another exemplary embodiment of an ablation device 100. The ablation device 100 is similar to the ablation device 10 described above and includes a tubular member 112 having a distal portion 114 and a proximal portion 116. The ablation device 100 may also include a distal cap 122. The distal cap 122 connects to a distal end 128 of the tubular member 112. The distal cap 122 may include an opening 123 having a diameter $d_1$ that is smaller than the diameter $d_2$ of the distal end portion 29 of the endoscope 31 referenced above and shown in FIG. 3. The ablation device 100 also may include a proximal ring 124 at a proximal end 134 of the tubular member 112 and a central ring 135 positioned distal to the proximal ring 124 and proximal to the end cap 122.

The ablation device 100 may also include a tensioning catheter 138 that is connected to the distal cap 122. Similar to the embodiments described above, a distal end 142 of the tensioning catheter 138 may extend distal to the distal cap 122 or may extend to the distal cap 122. The tensioning catheter 138 may include a lumen similar to the embodiments described above where a wire guide may be extended through the lumen of the tensioning catheter 138 to facilitate positioning of the ablation device 100 within a patient's lumen.

As shown in FIGS. 6 and 7, the ablation device 100 may also include a pushing catheter 152 and an over catheter 154. A distal end portion 156 of the pushing catheter 152 may extend through the proximal ring 124 and be connected to the central ring 135. The pushing catheter 152 may be movably positionable through the over catheter 154 so that the pushing catheter 152 can move the central ring 135 relative to the distal cap 122. The outer catheter 154 may be connected to the proximal ring 124 and may be positioned outside the endoscope as described above.

The pushing catheter 152 may be used to hold the tubular member 112 against the distal portion 29 of the endoscope 31 as the ablation device 100 is advanced or retracted through a patient's lumen similar to the ablation device 10 described above. The proximal ring 124 and the central ring 135 may be movably positionable over the distal portion 29 of the endoscope 31. The tensioning catheter 138 and/or the pushing catheter 152 may be used to hold the ablation device 100 against the endoscope 31 in the first configuration 140 as shown in FIG. 6 (without the endoscope). FIG. 7 illustrates the tubular member 112 in a second, expanded configuration 144. As shown, the pushing catheter 152 is advanced distally to move the central ring 135 relative to the distal cap 122. The tubular member 112 expands to the second configuration 144 as the central ring 135 is moved distally by the pushing catheter 152. The proximal ring 124 may also be moved distally as the tubular member 112 expands. Similar to the embodiments described above, any amount of movement of the central ring 135 to the distal cap 122 may be provided to expand the tubular member 112 any amount to the second configuration 144. The amount of expansion of the tubular member 112 will depend on the size of the body lumen into which the ablation device 100 is positioned. The pushing catheter 152 and/or the tensioning catheter 138 may be locked in position using a handle (described below) so that the tubular member 112 in the expanded configuration 144 may be held constant as the treatment is being delivered to the body lumen. In some embodiments, the size and shape of the body lumen may be increasing or decreasing as the ablation device 100 is advanced so the tubular member 112 may be changed in diameter during treatment or when the tubular member 112 is positioned at another site. The tubular member 112 may also be locked in the first configuration 140 for delivery to the treatment site and for repositioning.

In some embodiments, the proximal ring 124 and the central ring 135 may be configured change in size as the tubular member 112 expands and collapses. For example, in some embodiments, the proximal ring 124 and/or the central ring 135 may expand as the pushing catheter 152 advances the central ring 135 distally toward the distal cap 122. The proximal ring 124 and/or the central ring 13 may decrease in diameter as the pushing catheter 152 moves the central ring 135 proximally relative to the distal cap 122. In some embodiments, the proximal ring 124 and the central ring 135 remain the same diameter as the central ring 135 is advanced and the tubular member 112 expands. In some embodiments, the distal cap 122 may be configured to change diameter when the tubular member 112 is expanded. In some embodiments, the distal cap 122 may be configured to remain the same diameter when the tubular member 112 is expanded and collapsed. In some embodiments, the tubular member 112 may be moved distally so that the distal cap 122 may be moved proximally relative to the central ring 135 and or the proximal ring 124 to expand the tubular member 112

Figure 8:
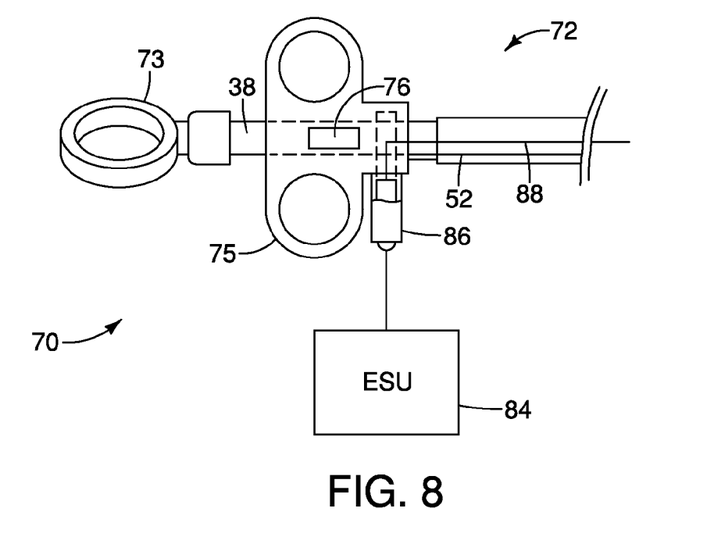
FIG. 8 is side view of an embodiment of a handle.

An exemplary control handle 70 is shown in FIG. 8 and will be described with reference to the ablation device 10, although the control handle 70 may also be used with the ablation device 100. One skilled in the art will recognize that other types of handles suitable for moving the pushing catheter 52, 152 relative to the tension catheter 38, 138 may also be used. The control handle 70 is provided at a proximal portion 72 of the ablation device 10. By way of non-limiting example, the handle 70 includes a first portion 73 and a second portion 75 that move relative to each other. In some embodiments, the first portion 73 may be operably connected to the tension catheter 38 and the second portion 75 may be operably connected to the pushing catheter 52. The first portion 73 may be moved proximally and/or the second portion 75 may be moved distally to move the pushing catheter 52 relative to the tensioning catheter 38 to move the tubular member 12 between the first and second configurations 40, 44.

The handle 70 may include a lock 76 to releasably lock the first portion 73 in position relative to the second portion 75 and thus lock the tubular member 12 in position. The lock 76 may releasably lock the first and second portions 73, 75 of the handle 70 together at any proximal/distal positioning of the pushing and tensioning catheters 52, 38 so that the tubular member 12 may be locked at any size and any position that is suitable for the treatment site. FIG. 8 also illustrates an energy source 84. The handle 70 may include a connector 86 for operably connecting one or more wires 88 to the energy source 84 to operably connect the energy source 84 to at least a portion of the tubular member 12 for treatment of the tissue. In some embodiments, the energy source 84 may be an electrical surgical unit. However, other types of energy sources 84 may also be used to provide energy to the tubular member 12. By way of non-limiting example, possible energy sources may include radiofrequency, microwave, ultraviolet, cryogenic and laser energies.

Figure 9A:
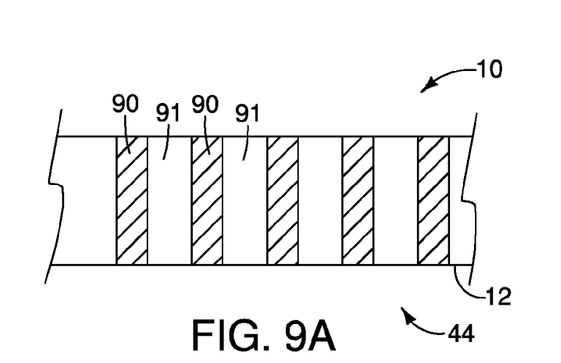
FIGS. 9A-9C illustrate partial views of an embodiment of a tubular member of an ablation device showing a conductive portion.
Figure 9B:
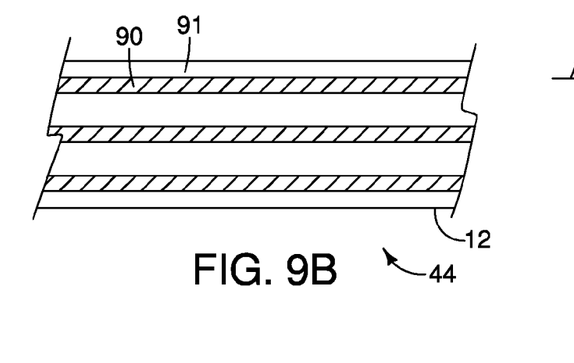
Figure 9C:
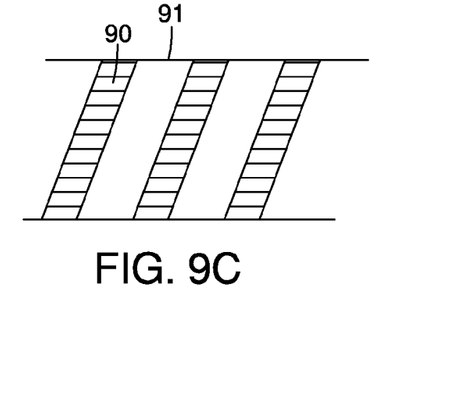

In some embodiments, the ablation device 10, 100 may be provided as a monopolar device where the tubular member is energized and return portion is provided elsewhere. In some embodiments the ablation device 10, 100 may be provided as a bipolar device. The features describe below with reference to the ablation device 10 may also be included with the ablation device 100. In some embodiments, the tubular member 12 includes a conductive portion 90 that is operatively connected to the wire 88 (See FIG. 8). The tubular member 12 itself, when formed from an electrically conductive material, may be the conductive portion 90 or portions of the tubular member 12 may be conductive portions 90 with non-conductive portions 91 being positioned between conductive portions 90. In some embodiments, the non-conductive portions 91 may be coated with an insulating material. For example, in a bipolar ablation device 10, an insulating material may be used between the active and return portions. The insulating material can also be used to form patterns for ablation, where conductive portions 90 of the tubular member 12 may be activated and non-conductive portions 90 of the tubular member 12 remain inactive. See for example, FIG. 9A-9C illustrating embodiments of the ablation device 10 showing the tubular member 12 having conductive portions 90 separated by non-conductive portions 91. The non-conductive portions 91 may be provided between conductive portions 90 of the tubular member 12 and the space between the conductive portions 90 may be optimized to control the depth of ablation of the target tissue. Spacing distances between the conductive portions 90 may be optimized depending on such factors as the type of target tissue, the depth of the lesion, the type of energy and the length of application of the energy to the tissue. The pattern of the conducting portions 90 may also vary.

In some embodiments, the conductive portions 90 of the tubular member 12 may comprise conductive ink that is applied to the exterior of the tubular member 12. The conductive ink may be applied in any pattern and spacing to be used for tissue treatment. In some embodiments, the conductive ink may be a silver-based ink. An exemplary silver-based ink may be obtained from Conductive Compounds (product number AG-510, Hudson, N.H.). However, other types of conductive ink may also be used, such as platinum-based, gold-based and copper-based inks. The inks may be epoxy-based inks or non-epoxy inks, such as urethane inks. In some embodiments, the active portions of the mesh member 20 may comprise conductive polymers. The conductive ink may be applied to the mesh member 20 with a variety of printing processes, such as pad printing, ink jet printing, spraying, marker striping, painting or other like processes. In some embodiments, the conductive ink may be applied to the mesh member with by spraying, dipping, painting or an electrostatic coating process.

The non-conductive portion 91 of the tubular member 12 may be an insulating portion to separate conductive portions 90 of the tubular member. In some embodiments, a coating may be applied to the tubular member 12 to form the non-conductive portions 91 in a quantity that is sufficient to insulate the conductive portions 90 from each other or to coat portions of the tubular member 12 when the tubular member 12 itself is formed of a conductive material. In some embodiments, the insulating coating may be made from parylene-N (poly-p-xylylene). Other xylylene polymers, and particularly parylene polymers, may also be used as a coating within the scope of the present invention, including, for example, 2-chloro-p-xylylene (Parylene C), 2,4-di-chloro-p-xylylene (Parylene D), poly(tetraflouro-p-xylylene), poly(carboxyl-p-xylylene-co-p-xylylene), fluorinated parylene, or parylene HT®(a copolymer of perfluorinated parylene and non-fluorinated parylene), alone or in any combination. Preferred coatings will include the following properties: low coefficient of friction (preferably below about 0.5, more preferably below about 0.4, and most preferably below about 0.35); very low permeability to moisture and gases; fungal and bacterial resistance; high tensile and yield strength; high conformality (ready application in uniform thickness on all surfaces, including irregular surfaces, without leaving voids); radiation resistance (no adverse reaction under fluoroscopy); bio-compatible/bio-inert; acid and base resistant (little or no damage by acidic or caustic fluids); ability to be applied by chemical vapor deposition bonding/integrating to wire surface (bonding is intended to contrast to, for example, fluoroethylenes that form surface films that are able to be peeled off an underlying wire); and high dielectric strength.

In some embodiments, the tubular member 12 or portions thereof may be formed from wire such as nickel titanium alloys, for example, nitinol, stainless steel, cobalt alloys and titanium alloys. In some embodiments, the tubular meber 12 or portions thereof may be formed from a polymeric material such as a polyolefin, a fluoropolymer, a polyester, for example, polypropylene, polytetrafluoroethylene, polyvinylidene fluoride, polyethylene terephthalate (PET), and combinations thereof. Other materials known to one skilled in the art may also be used to form the tubular member 12.

Figure 10A:
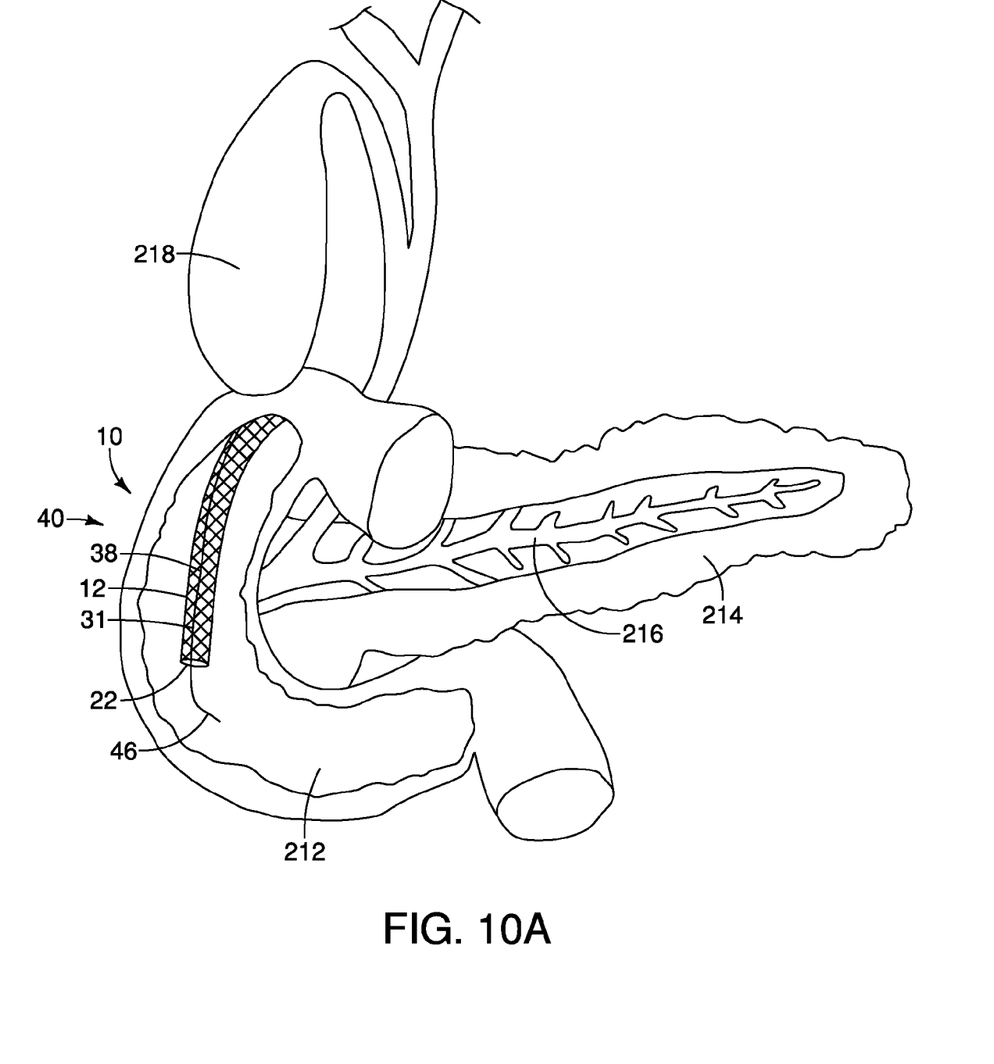
FIGS. 10A and 10B illustrate operation of an embodiment of an ablation device.

Operation of the ablation device 10, 100 will be explained with reference to FIGS. 10A and 10B using the ablation device 10 as an example being delivered to the gastrointestinal tract. FIG. 10A illustrates the ablation device 10 being delivered to a treatment site within the duodenum 212. The pancreas 214, the pancreatic duct 216 and the gall bladder 218 are also shown for reference. As shown in FIG. 10A, the ablation device 10 is positioned over the endoscope 31 in the first configuration 40 for delivery to the treatment site. The distal cap 22 is positioned distal to the endoscope 31 and the tubular member 12 is positioned close to the endoscope 31. The tensioning catheter 38 is positioned in the working channel of the endoscope 31 and connected to the distal cap 22. The ablation device 10 has been delivered to the duodenum 212 over the wire guide 46 that is shown extending from the lumen 43 of the tensioning catheter 38.

Figure 10B:
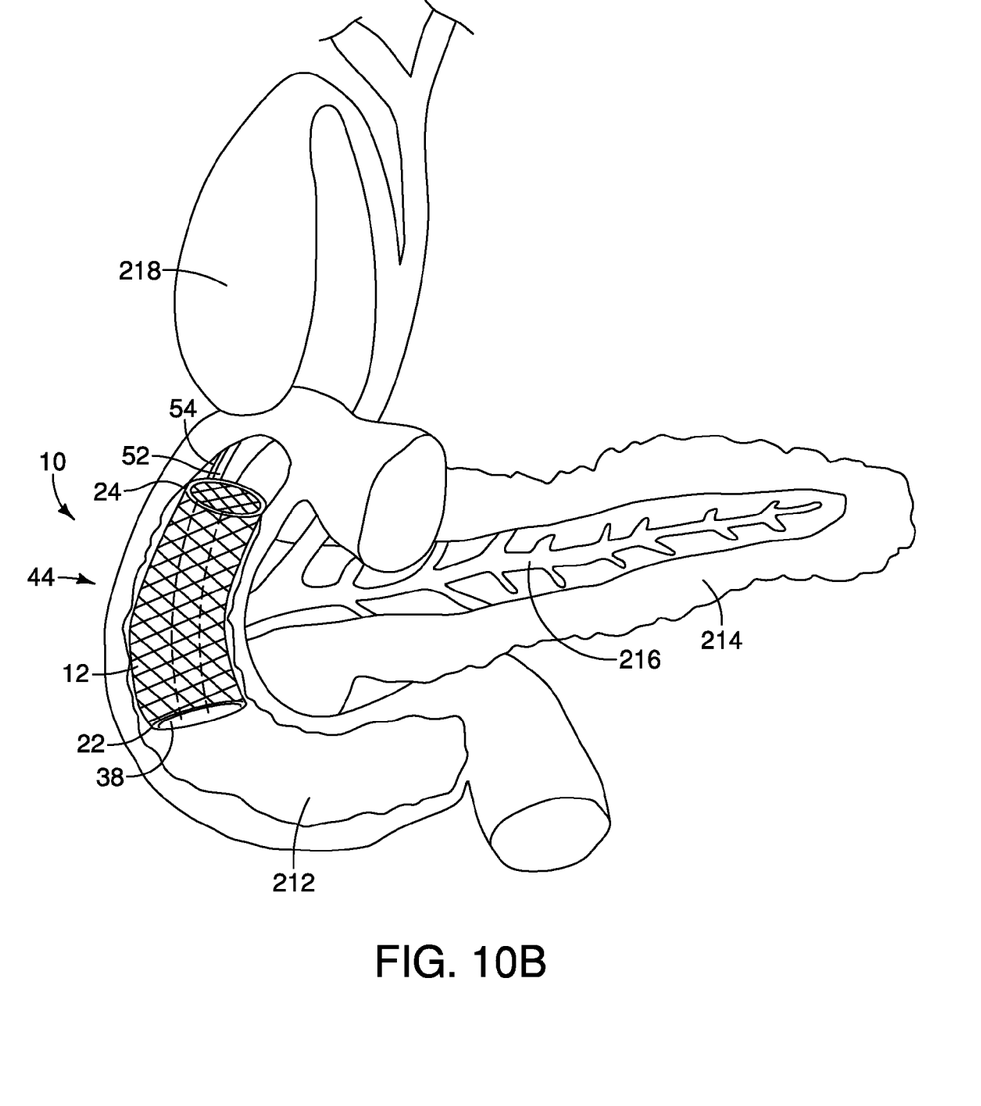

FIG. 10B illustrates the ablation device 10 in the second configuration 44 so that the tubular member 12 is expanded to contact the walls of the duodenum 212. As shown in FIG. 10B, the proximal ring 24 has been moved relative to the distal cap 22 so that the proximal ring 24 and the distal cap 22 are positioned closer together. In the embodiment shown, the pushing catheter 52 within the outer catheter 54 has moved the proximal ring 24 distally toward the distal cap 22 to expand the tubular member 12. The tensioning catheter 38 connected to the distal cap 22 may be used to hold the distal cap 22 in position or to proximally pull the distal cap 22 toward the proximal ring 24 to facilitate expansion of the tubular member 12.

Once the tubular member 12 is properly positioned at the treatment site, the handle 70 may be locked to keep the ablation device in the second configuration during treatment. The power source 84 is activated for a sufficient time to treat the tissue. The handle 70 may be unlocked and the tubular member 12 positioned in the first configuration by proximally withdrawing the proximal ring 24 using the pushing catheter 54 and/or distally moving the distal cap 22 with the tensioning catheter 38. The tubular member 12 may then be repositioned at another treatment site and returned to the second configuration 44. Once the treatment is complete, the ablation device 10 and the endoscope 31 may be withdrawn. While the procedure has been described with reference to the treatment within the duodenum, the location of the treatment is not limited to the duodenum. By way of non-limiting example, portions of the stomach, the gastro-intestinal tract, the esophagus the lungs or the vascular system may also be treated using the ablation device 10.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. An ablation device comprising:
   a tubular member having a proximal portion, a distal portion and a lumen extending at least partially therethrough, the tubular member having a first configuration and a second configuration, the tubular member comprises a conductive portion;
   a distal cap operably connected to the distal portion, the cap having a diameter that is smaller than a diameter of a distal end portion of an endoscope;
   a proximal ring connected to the proximal portion, the proximal ring comprising a first portion and a second portion spaced apart from the first portion on a circumference of the proximal ring, the proximal ring having a diameter greater than a diameter of the distal end portion so that the proximal ring is sized and shaped to fit over the distal end portion;
   a tensioning member operably connected to the distal cap;
   a pushing member operably connected to the proximal ring at the first portion on the circumference of the proximal ring and the proximal ring at the second portion being free from connection to the pushing member; and
   an over catheter having the pushing member at least partially extending through a lumen of the over catheter;
   wherein the proximal ring is movable relative to the distal cap to move the tubular member between the first configuration and the second confirmation.

2. The ablation device according to claim 1, wherein the tubular member comprises a mesh.

3. The ablation device according to claim 1, further comprising a central ring positioned between the proximal ring and the distal cap.

4. The ablation device according to claim 1, further comprising a handle operatively connected to the tensioning member and the pushing member.

5. The ablation device according to claim 1, wherein at least a portion the lumen of the tubular member has a diameter greater than the distal end portion of the endoscope.

6. The ablation device according to claim 1, wherein the over catheter is adapted to be connected to the distal end portion of the endoscope.

7. The ablation device according to claim 1, wherein the tensioning member comprises a lumen extending at least partially therethrough.

8. The ablation device according to claim 7, further comprising a wire guide extending through at least a portion of the lumen of the tensioning member.

9. The ablation device according to claim 1, wherein the proximal ring is expandable so that the proximal ring has a first diameter in a first configuration and a second diameter in a second configuration, the second diameter being greater than the first diameter.

10. The ablation device according to claim 1, wherein the tubular member comprises a plastic material.

11. The ablation device according to claim 1, wherein the conductive portion comprises a conductive ink.

12. The ablation device according to claim 1, wherein the ablation device is a bipolar device.

13. The ablation device according to claim 1, wherein the tubular member comprises a non-conductive portion.

14. The ablation device according to claim 1, wherein the conductive portion comprises a plurality of conductive regions, each of the plurality of conductive regions being independently energizable.

15. The ablation device according to claim 1, wherein the tensioning member is adapted to extend through a working channel of the endoscope and to connects to the distal cap.

16. A method of ablating a tissue, the method comprising:
   inserting a distal portion of an endoscope into a lumen of a patient, the distal portion having an ablation device positioned over at least a portion of the distal portion, the ablation device comprising:
   a tubular member having a proximal portion, a distal portion and a lumen extending at least partially therethrough, the tubular member having a first configuration and a second configuration, the tubular member comprises a conductive portion;
   a distal cap operably connected to the distal portion, the cap having a diameter that is smaller than a diameter of a distal end portion of an endoscope;
   a proximal ring connected to the proximal portion, the proximal ring comprising a first portion and a second portion spaced apart from the first portion on a circumference of the proximal ring, the proximal ring having a diameter greater than a diameter of the distal end portion so that the proximal ring is sized and shaped to fit over the distal end portion;
   a tensioning member operably connected to the distal cap;
   a pushing member operably connected to the proximal ring at the first portion on the circumference of the proximal ring and the proximal ring at the second portion being free from connection to the pushing member; and
   an over catheter having the pushing member at least partially extending through a lumen of the over catheter;
   wherein the proximal ring is movable relative to the distal cap to move the tubular member between the first configuration and the second confirmation; and
   applying energy to the tissue from an energy source.

17. The method according to claim 16, comprising distally moving the proximal ring toward the distal cap to move the ablation device to the second configuration so that at least a portion of the tubular member is expanded away from the distal portion of the endoscope.

18. The method according to claim 16, comprising distally moving a central ring toward the distal cap.

19. The method according to claim 16, comprising extending the tensioning member through a working channel of the endoscope.

20. The method according claim 16, comprising operably connecting the over catheter to the endoscope.

* * * * *

UNITED STATES PATENT AND TRADEMARK OFFICE
CERTIFICATE OF CORRECTION

PATENT NO. : 9,615,880 B2
APPLICATION NO. : 14/327239
DATED : April 11, 2017
INVENTOR(S) : Shaun D. Gittard et al.

Page 1 of 1

It is certified that error appears in the above-identified patent and that said Letters Patent is hereby corrected as shown below:

In the Claims

In Column 10, Claim 15, Line 20, after "endoscope and to" replace "connects" with --connect--.

In Column 10, Claim 20, Line 64, after "The method according" insert --to--.

Signed and Sealed this
First Day of May, 2018

Andrei Iancu
*Director of the United States Patent and Trademark Office*